United States Patent [19]

Taniguchi et al.

[11] Patent Number: 5,082,856

[45] Date of Patent: Jan. 21, 1992

[54] PYRROLECARBOXYLIC ACID DERIVATIVES

[75] Inventors: Masao Taniguchi, Machida; Kohei Umezu, Yokohama; Tadashi Shirasaka, Machida; Shinya Inoue; Tetsuro Shinpuku, both of Yokohama; Masayuki Mitsuka, Machida; Mayumi Hirata, Yokohama, all of Japan

[73] Assignee: Mitsubishi Kasei Corporation, Tokyo, Japan

[21] Appl. No.: 369,816

[22] Filed: Jun. 22, 1989

[30] Foreign Application Priority Data

Jun. 23, 1988 [JP] Japan .................................. 63-155689
Dec. 22, 1988 [JP] Japan .................................. 63-324469
Apr. 7, 1989 [JP] Japan .................................. 1-88512
May 31, 1989 [JP] Japan .................................. 1-137644

[51] Int. Cl.$^5$ .................. A61K 31/40; C07D 207/333
[52] U.S. Cl. ...................................... 514/423; 548/531; 548/532; 548/535
[58] Field of Search .................. 548/532, 535, 531; 514/423

[56] References Cited

U.S. PATENT DOCUMENTS

| | | | |
|---|---|---|---|
| 2,479,971 | 8/1949 | Scholz | 548/531 |
| 2,479,972 | 8/1949 | Scholz | 548/535 |
| 2,500,713 | 3/1950 | Sickels et al. | 548/531 |
| 4,194,003 | 3/1980 | LaForest et al. | 514/423 |
| 4,560,700 | 12/1985 | Schnettler et al. | 514/423 |
| 4,824,958 | 4/1989 | Cetenko et al. | 548/532 X |

FOREIGN PATENT DOCUMENTS 58-85861 5/1983 Japan .................................. 548/532

Primary Examiner—Joseph P. Brust
Attorney, Agent, or Firm—Oblon, Spivak, McClelland, Maier & Neustadt

[57] ABSTRACT

Novel pyrrolecarboxylic acid derivatives represented by the following formula:

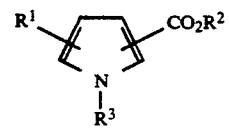

where $R^1$ is a hydrogen atom, an alkyl group of 5 to 25 carbon atoms or an alkenyl group of 5 to 25 carbon atoms, $R^2$ is a hydrogen atom, a phenyl group or an optionally substituted alkyl group of 1 to 10 carbon atoms, and $R^3$ is a hydrogen atom, an alkyl group of 5 to 25 carbon atoms or an alkenyl group of 5 to 25 carbon atoms, or pharmaceutically acceptable salts thereof are provided.

The compounds are highly effective in reducing the level of triglyceride or cholesterol in serum, and useful as an active ingredient of a pharmaceutical composition for treating hyperlipemia and arteriosclerosis.

12 Claims, No Drawings

PYRROLECARBOXYLIC ACID DERIVATIVES

FIELD OF THE INVENTION

This invention relates to pyrrolecarboxylic acid derivatives or pharmaceutically acceptable salts thereof which are potent in reducing lipids and, therefore, useful as a therapeutical medicine for hyperlipemia.

BACKGROUND OF THE INVENTION

Heretofore, it has been considered that a metabolic error of lipids in blood, such as triglyceride or cholesterol, is one of the major dangerous factors causing an abnormal increase in or imbalance of the level of lipids in blood, which results in arteriosclerosis as well as ischemic heart disease such as angina pectoris or myocardial infarction, and cerebral infarction.

As a medicine for hyperlipemia, clofibrate type medicine, nicotinic acid and derivative thereof have been mainly used so far. Although they reduce the level of triglycerides in blood, they are less effective in reducing the cholesterol. Further, probucol having a new structure or cholestyramine which is an anion exchange resin, has been used in recent years as the medicine for reducing the blood level of cholesterol, but they are contrarily inactive to the triglyceride.

The abnormal increase in the blood level of either triglyceride or cholesterol is a major factor in arteriosclerosis, in particular, atherosclerosis. It has especially been known that the risk of the onset of those diseases is remarkably increased if both types of lipids are increased simultaneously.

As described in the foregoing, although the medicines for reducing the level of triglycerides or cholesterol in blood have already been used clinically, it is further demanded to develop a more potent medicine which has little adverse reaction and is preferable also in the dosage, safety and application. In particular, much attention has been focused to the development of a medicine capable of effectively reducing both of the levels of triglycerides and cholesterol in blood together in view of the therapy and prevention of diseases caused by arteriosclerosis, such as ischemic heart disease and cerebral infarction, but no such medicine capable of satisfying these requirements has yet been found.

SUMMARY OF THE INVENTION

It has been found in the present invention that a specific class of pyrrolecarboxylic acid derivative or pharmaceutically acceptable salt thereof is potently effective in reducing both of the levels of triglycerides and cholesterol in blood as compared to the conventional medicines.

Specifically, the present invention provides pyrrolecarboxylic acid derivatives represented by the following formula (I):

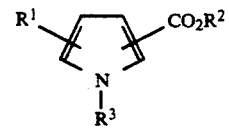

wherein $R^1$ is a hydrogen atom, an alkyl group of 5 to 25 carbon atoms or an alkenyl group of 5 to 25 carbon atoms, $R^2$ is a hydrogen atom, a phenyl group or an optionally substituted alkyl group of 1 to 10 carbon atoms and $R^3$ is a hydrogen atom, an alkyl group of 5 to 25 carbon atoms or an alkenyl group of 5 to 25 carbon atoms, or pharmaceutically acceptable salts thereof.

The pyrrolecarboxylic acid derivatives or salts thereof in accordance with the invention are highly potent in reducing the level of triglycerides and cholesterol in blood, and accordingly useful as an active ingredient of a pharmaceutical composition for treating hyperlipemia and arteriosclerosis.

DETAILED DESCRIPTION OF THE PREFERRED EMBODIMENTS

In the formula (I), as the alkyl group of $R^1$ or $R^3$, there can be mentioned a linear or branched group of 5 to 25 carbon atoms, preferably, an alkyl group of 10 to 16 carbon atoms. Further, as the alkenyl group of $R^1$ or $R^3$, there can be mentioned an alkenyl group of 5 to 25 carbon atoms having at least one vinyl group in the molecule, preferably, an alkenyl group of 10 to 16 carbon atoms. $R^1$ or $R^3$ can also be cycloalkyl of 5 to 25 carbon atoms.

In the formula (I), as the alkyl group of $R^2$, there can be mentioned an alkyl group of 1 to 10 carbon atoms, particularly, an alkyl group of 1 to 4 carbon atoms. Examples of a substituent optionally present in the alkyl group of $R^2$ include a halogen atom, hydroxyl group, amino group, carbamoyl group, alkylamino group of 1 to 5 carbon atoms, dialkylamino group of 2 to 10 carbon atoms, alkylcarbonylamino group of 1 to 5 carbon atoms, alkylthio group of 1 to 5 carbon atoms, mercapto group, alkylcarbonyloxy group of 1 to 5 carbon atoms and aminocarbonyloxy group.

In the present invention, the compounds in which the substituents $R^1$ and $-CO_2R^2$ are present at such positions not adjacent to each other on the pyrrole ring are preferred from the view point of the activity. More specifically, the preferred compounds are those wherein $-CO_2R^2$ is present at 3-position, in which $R^2$ is preferably a hydrogen atom, and $R^1$ is present at 5-position on the pyrrole ring, or those wherein $-CO_2R^2$ is present at 2-position, in which $R^2$ is preferably a hydrogen atom, and $R^1$ is present at 4- or 5-position on the pyrrole ring.

Further, those compounds in which one of the substituents $R^1$, $R^2$ or $R^3$ is a hydrogen atom are also preferred. The examples of the preferred compounds according to the invention are tabulated in Table 1 below.

TABLE 1

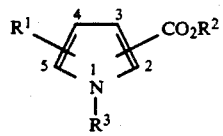

| Compd. No. | Position of $R^1$ | $R^1$ | Position of $CO_2R^2$ | $R^2$ | $R^3$ |
|---|---|---|---|---|---|
| 1 | 4 | $CH_3(CH_2)_4-$ | 2 | H | H |
| 2 | 5 | $CH_3(CH_2)_5-$ | 3 | " | " |
| 3 | 4 | $CH_3(CH_2)_6-$ | 2 | " | " |
| 4 | 5 | $CH_3(CH_2)_7-$ | 3 | " | " |
| 5 | 4 | $CH_3(CH_2)_8-$ | 2 | " | " |
| 6 | 5 | $CH_3(CH_2)_9-$ | 3 | " | " |
| 7 | 4 | " | 2 | " | " |
| 8 | 5 | $CH_3(CH_2)_{10}-$ | 3 | " | " |
| 9 | 4 | " | 2 | " | " |
| 10 | " | $CH_3(CH_2)_{11}-$ | " | " | " |
| 11 | " | " | 2 | $-CH_3$ | " |
| 12 | 5 | " | 3 | " | " |
| 13 | " | " | " | H | " |
| 14 | 4 | $CH_3(CH_2)_{12}-$ | 2 | " | " |
| 15 | " | " | " | $-CH_3$ | " |
| 16 | " | " | " | $-C_2H_5$ | " |
| 17 | " | " | " | $-C_3H_7$ | " |
| 18 | " | " | " | $-C_4H_9$ | " |
| 19 | 5 | $CH_3(CH_2)_{12}-$ | 3 | $-C_2H_5Br$ | H |
| 20 | " | " | " | $-C_2H_5OH$ | " |
| 21 | " | " | " | $-CH_2CH_2N(CH_3)_2$ | " |
| 22 | " | " | " | $-CH_2CH_2NH_2$ | " |
| 23 | 4 | " | 2 | $-CH_2NHCOCH_3$ | " |
| 24 | " | " | " | $-CH_2SCH_3$ | " |
| 25 | " | " | " | $-CH_2CH_2SH$ | " |
| 26 | 5 | " | 3 | $-CH_2OCOCH_3$ | " |
| 27 | " | " | " | $-CH_2OCOC(CH_3)_3$ | " |
| 28 | " | " | 2 | $-CH_2OCONH_2$ | " |
| 29 | 4 | " | " | Ph | " |
| 30 | 5 | " | 3 | H | " |
| 31 | " | " | " | $-CH_3$ | " |
| 32 | " | " | " | $-C_2H_5$ | " |
| 33 | 4 | " | 2 | $-(CH_2)_2N(CH_3)_2$ | " |
| 34 | " | " | " | $-CH_2CONHC_4H_9$ | " |
| 35 | " | " | " | $-CH_2CON(C_2H_5)_2$ | " |
| 36 | " | " | " | $-CH_2CON(CH_2CH_2OH)_2$ | " |
| 37 | " | $CH_3(CH_2)_{13}-$ | " | H | " |
| 38 | 5 | " | 3 | " | " |
| 39 | 4 | " | 2 | $-CH_3$ | " |
| 40 | 5 | " | " | H | " |
| 41 | 5 | $CH_3(CH_2)_{13}-$ | 2 | $-C_2H_5$ | H |
| 42 | " | " | 3 | " | " |
| 43 | " | " | " | $-C_3H_7$ | " |
| 44 | 4 | " | 2 | $-C_4H_9$ | " |
| 45 | " | $CH_3(CH_2)_{14}-$ | " | H | " |
| 46 | " | " | " | $-CH_3$ | " |
| 47 | 5 | $CH_3(CH_2)_{15}-$ | 3 | H | " |
| 48 | " | " | " | $-CH_3$ | " |
| 49 | 4 | $CH_3(CH_2)_{16}-$ | 2 | H | " |
| 50 | " | " | " | $-CH_3$ | " |
| 51 | " | $CH_3(CH_2)_{17}-$ | " | H | " |
| 52 | " | $CH_3(CH_2)_{18}-$ | " | " | " |
| 53 | 5 | $CH_3(CH_2)_{19}-$ | 3 | " | " |
| 54 | " | $CH_3(CH_2)_{20}-$ | " | " | " |
| 55 | " | $CH_3(CH_2)_{21}-$ | " | " | " |
| 56 | " | $CH_3(CH_2)_{22}-$ | " | " | " |
| 57 | " | $CH_3(CH_2)_{23}-$ | " | " | " |
| 58 | 4 | $CH_3(CH_2)_7-$ | 2 | $CH_3$ | H |
| 59 | " | $CH_3(CH_2)_8-$ | " | " | " |
| 60 | " | $CH_3(CH_2)_9-$ | " | " | " |
| 61 | 5 | $CH_3(CH_2)_{10}-$ | 3 | " | " |
| 62 | 4 | $(CH_3)_3C(CH_2)_5-$ | 2 | H | " |
| 63 | " | $(CH_3)_3C(CH_2)_8-$ | " | " | " |
| 64 | 5 | $CH_3C(CH_3)_2(CH_2)_{11}-$ | 3 | " | " |
| 65 | " | $CH_3(CH_2)_5C(CH_3)_2(CH_2)_5-$ | " | " | " |
| 66 | " | 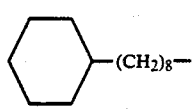 | " | " | " |

TABLE 1-continued

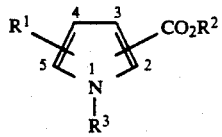

| Compd. No. | Position of $R^1$ | $R^1$ | Position of $CO_2R^2$ | $R^2$ | $R^3$ |
|---|---|---|---|---|---|
| 67 | " | $CH_3(CH_2)_7CH=CH(CH_2)_8-$ | " | " | " |
| 68 | " | $CH_3(CH_2)_4CH=CH-CH_2CH=CH-(CH_2)_8-$ | 2 | " | " |
| 69 | 4 | $CH_3(CH_2CH=CH)_3-(CH_2)_8-$ | " | " | " |
| 70 | 5 | $(CH_3)_2C=CH-(CH_2)_2-C(CH_3)=CH-(CH_2)_2-C(CH_3)=CH-CH_2-$ | " | " | " |
| 71 | " | $(CH_3)_2C=CH-(CH_2)_2-C(CH_3)=CH-CH_2-$ | " | " | " |
| 72 | 4 | $CH_3(CH_2)_{10}CH=CH-$ | 2 | " | " |
| 73 | " | " | " | $-CH_3$ | " |
| 74 | " | $CH_3(CH_2)_{11}CH=CH-$ | " | " | " |
| 75 | " | " | " | H | " |
| 76 | 5 | $CH_3(CH_2)_{12}CH=CH-$ | 3 | " | " |
| 77 | " | " | " | $-CH_3$ | " |
| 78 | 5 | $CH_3(CH_2)_{13}CH=CH-$ | 3 | H | H |
| 79 | " | $CH_3(CH_2)_{14}CH=CH-$ | " | " | " |
| 80 | — | H | " | " | $CH_3(CH_2)_7-$ |
| 81 | " | " | " | $-C_2H_5$ | " |
| 82 | " | " | " | H | $CH_3(CH_2)_8-$ |
| 83 | " | " | " | $-C_2H_5$ | " |
| 84 | " | " | " | H | $CH_3(CH_2)_9-$ |
| 85 | " | " | " | $-C_2H_5$ | " |
| 86 | " | " | " | H | $CH_3(CH_2)_{10}-$ |
| 87 | " | " | " | $-C_2H_5$ | " |
| 88 | " | " | " | H | $CH_3(CH_2)_{11}-$ |
| 89 | " | " | " | $-C_2H_5$ | " |
| 90 | " | " | " | H | $CH_3(CH_2)_{12}-$ |
| 91 | " | " | " | $-C_2H_5$ | " |
| 92 | " | " | " | H | $CH_3(CH_2)_{13}-$ |
| 93 | " | " | " | $-C_2H_5$ | " |
| 94 | " | " | " | H | $CH_3(CH_2)_{14}-$ |
| 95 | " | " | " | $-C_2H_5$ | " |
| 96 | " | " | " | H | $CH_3(CH_2)_{15}-$ |
| 97 | " | " | " | $-C_2H_5$ | " |
| 98 | " | " | " | H | $CH_3(CH_2)_{16}-$ |
| 99 | " | " | " | $-C_2H_5$ | " |
| 100 | — | H | 3 | H | $CH_3(CH_2)_{17}-$ |
| 101 | " | " | " | $-C_2H_5$ | " |
| 102 | " | " | " | H | $CH_3CH_2CH=CH(CH_2)_{10}-$ |
| 103 | " | " | " | $-C_2H_5$ | $CH_3CH_2CH=CH(CH_2)_{10}-$ |
| 104 | " | " | " | H | $CH_3(CH_2)_3CH=CH(CH_2)_{10}-$ |
| 105 | " | " | " | $-C_2H_5$ | " |
| 106 | 5 | $CH_3(CH_2)_{11}-$ | " | H | $CH_3(CH_2)_6-$ |
| 107 | " | $CH_3(CH_2)_{12}-$ | " | " | " |
| 108 | " | " | " | " | $CH_3(CH_2)_7-$ |
| 109 | 4 | " | 2 | " | $CH_3(CH_2)_4-$ |
| 110 | " | " | " | " | $CH_3(CH_2)_8-$ |
| 111 | 5 | " | 3 | " | " |
| 112 | " | " | " | " | $CH_3(CH_2)_9-$ |
| 113 | " | " | " | " | $CH_3(CH_2)_{13}-$ |
| 114 | " | " | " | " | $CH_3(CH_2)_5-$ |
| 115 | 4 | " | 2 | " | " |
| 116 | " | " | " | " | $CH_3(CH_2)_6CH=CH-$ |
| 117 | 5 | $CH_3(CH_2)_{13}-$ | 3 | " | $CH_3(CH_2)_{10}CH=CH-$ |

The pharmaceutically acceptable salts of the pyrrolecarboxylic acid derivatives include, for example, inorganic salts of metal such as sodium, potassium, calcium or magnesium, and organic amine salts such as ammonium salts or triethylammonium salts, cyclohexylammonium salts, or lysine salts. Further, in a case where an amino group may be present in the group $R^2$ of the formula (I), there can also be mentioned salts of inorganic acid such as hydrochloric acid, hydrobromic acid and sulfuric acid, or salts of organic acid such as maleic acid, succinic acid or citric acid.

The compound of the present invention may be prepared, for example according to the processes described below.

Method 1:

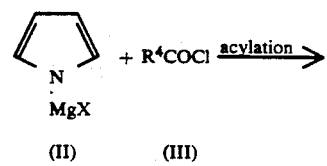

-continued

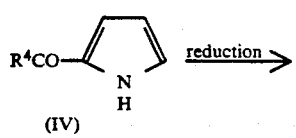

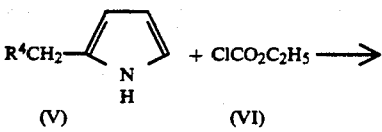

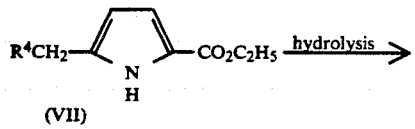

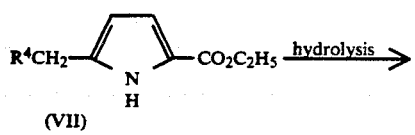

In the above formulae, R⁴ is an alkyl group of 4 to 24 carbon atoms and X is a halogen atom.

The compound (II) obtained by reacting pyrrole with a methyl or ethyl magnesium halide is treated with an appropriate acyl chloride (III) in an inert solvent such as diethyl ether or tetrahydrofuran to give 2-acylpyrrole (IV). When the compound (IV) is subjected to usual Wolff-Kishner reduction, 2-alkylpyrrole (V) is obtained at a high yield via the reduction of ketone group. The compound (V) is then treated in an inert solvent such as diethyl ether or tetrahydrofuran with a Grignard reagent and, further, reacted with ethyl chlorocarbonate (VI) at a temperature of from 0° C. to a boiling point of the solvent to give ethyl 5-alkylpyrrole-2-carboxylate (VII). The compound (VII) can be converted into the compound of the present invention represented by the formula (VIII) by hydrolyzing it in a conventional manner.

Method 2:

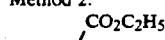

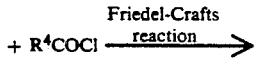

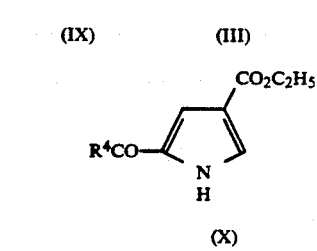

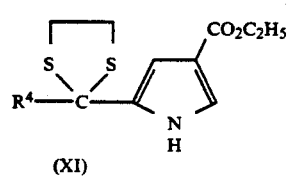

-continued

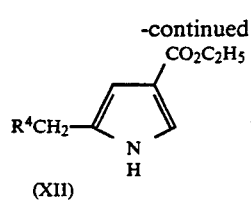

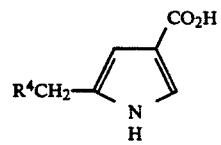

In the above formulae, R⁴ is an alkyl group of 4 to 24 carbon atoms.

Ethyl pyrrole-3-carboxylate (IX) is reacted with an appropriate acyl chloride (III) in the presence of a Lewis acid such as aluminium chloride, stannic chloride or boron trifluoride diethyl ether complex, in a solvent ordinarily used for Friedel-Crafts reaction such as benzene and carbon disulfide at a temperature of from −10° C. to the boiling point of the solvent to obtain ethyl 5-acyl-pyrrole-3-carboxylate (X). After converting the ketone group into a dithioketal (XI) in a usual manner, ethyl 5-alkylpyrrole-3-carboxylate (XII) is obtained by heating the dithioketal (XI) under reflux with an excess Raney nickel in a solvent, preferably, ethanol. Further, a conventional hydrolysis of the compound (XII) affords the compound of the invention of the formula (XIII). The compound (IX) may be prepared by a known method described in literatures (for example, Canadian Journal of Chemistry, vol. 58, p. 2527, 1980).

Method 3:

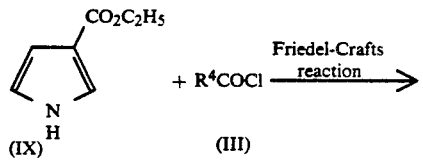

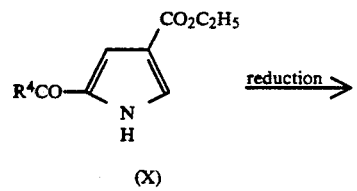

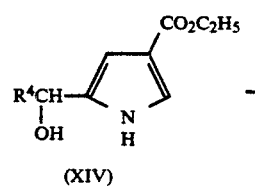

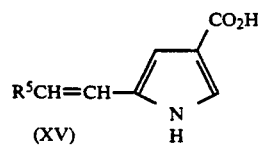

In the above formulae, $R^4$ is an alkyl group of 4 to 24 carbon atoms and $R^5$ is an alkyl group of 3 to 23 carbon atoms.

Ethyl 5-acylpyrrole-3-carboxylate (X) resulted in accordance with the above Method 2 is subjected to reduction in an alcoholic solvent such as methanol or ethanol using an appropiate reducing agent, preferably, sodium borohydride to give an alcoholic compound (XIV). The compound (XIV) is then heated under reflux together with an excess base such as sodium hydroxide or potassium hydroxide in an aqueous alcoholic solvent such as ethanol or ethylene glycol for an appropriate time to hydrolyze the ethyl carboxylate. At the same time, dehydration also takes place to give the compound of the present invention represented by the formula (XV).

Method 4:

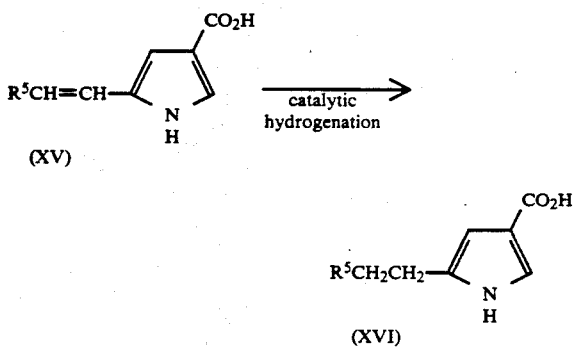

In the above formulae, $R^5$ is an alkyl group of 3 to 23 carbon atoms.

The compound (XV) having an alkenyl group with a double bond conjugated with the pyrrole ring obtained in the above Method 3 is subjected to catalytic hydrogenation in an appropriate solvent, for example, alcoholic solvent such as methanol or organic acid such as acetic acid, using palladium-black, palladium carbon, platinum or the like as a catalyst to give the compound according to the present invention represented by the formula (XVI).

Method 5:

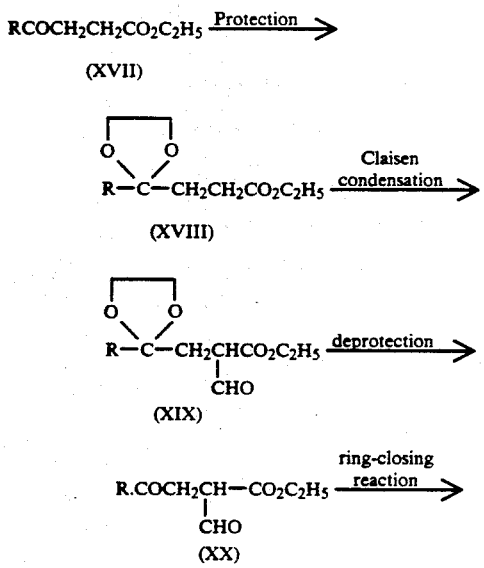

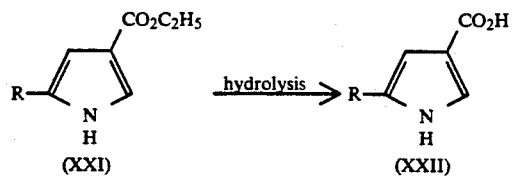

In the above formulae, R is an alkyl group of 5 to 25 carbon atoms.

After protecting the ketone group of the γ-ketoester (XVII) as an ethyleneketal in accordance with a conventional manner, the resultant compound (XVIII) is subjected to a so-called Claisen condensation together with ethyl formate in an inert solvent such as ether or tetrahydrofuran, in the presence of a base such as sodium hydride or sodium ethoxide to give the compound (XIX). Then, after deprotecting the ethyleneketal group, the resultant compound (XX) is reacted with ammonia or ammonium acetate in an alcoholic solvent to afford ethyl 5-alkylpyrrole-3-carboxylate (XXI) via pyrrole ring formation. Further, the compound (XXI) can be hydrolyzed according to the usual method into the compound represented by the formula (XXII) of the present invention. The starting γ-ketoester (XVII) can be synthesized by any known method described in literatures (for example, Chemical Abstract, vol. 81, 63104e; Ion (Madrid), Vol. 34, No. 397, p. 557, 1974).

Method 6:

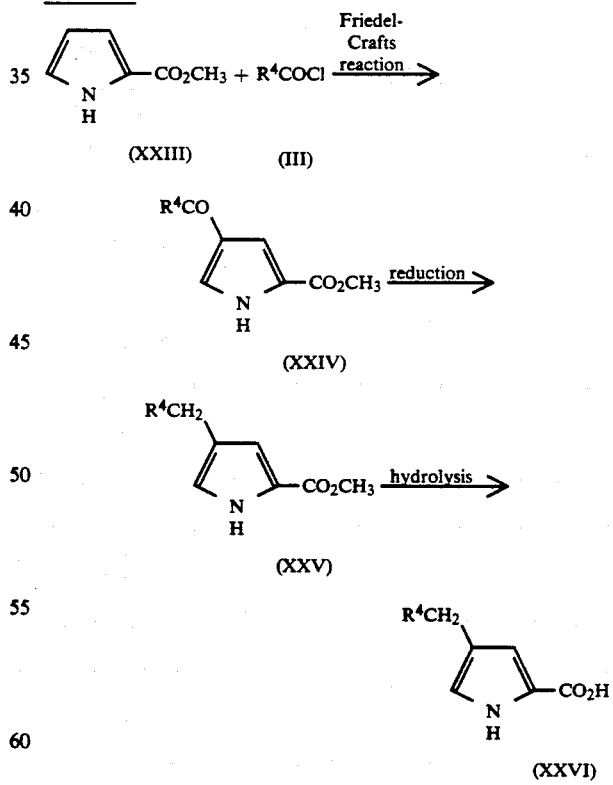

In the above formulae, $R^4$ is an alkyl group of 4 to 24 carbon atoms.

Methyl pyrrole-2-carboxylate (XXIII) is subjected to a Friedel-Crafts reaction with an appropriate acyl chloride (III) in the presence of a Lewis acid such as aluminum chloride, stannic chloride or boron trifluoride diethyl ether complex, in a solvent such as benzene or carbon disulfide at a temperature of from −10° C. to the boiling point of the solvent to give methyl 4-acylpyrrole-2-carboxylate (XXIV). Then, the keto group is subjected to an appropriate reduction, for example, diborane reduction, Raney nickel reduction for dithioketal described in the Method 2 to convert the compound (XXIV) into methyl 4-alkylpyrrole-2-carboxylate (XXV). Alternatively, the compound (XXIV) may be converted into the compound (XXV) by a catalytic hydrogenation of an acetate which is derived from the compound (XXIV) via an alcohol. Further, the compound (XXV) is conventionally hydrolyzed into 4-alkylpyrrole-2-carboxylic acid represented by the formula (XXVI).

Method 7:

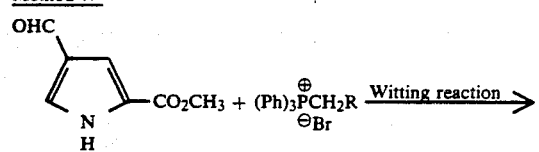

(XXVII)      (XXVIII)

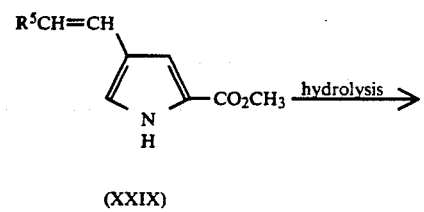

(XXIX)

$R^5CH=CH$ \\ —CO$_2$H (XXX)

In the above formulae, $R^5$ is an alkyl group of 3 to 23 carbon atoms.

Wittig reaction between methyl 4-formylpyrrole-2-carboxylate of the formula (XXVII) (Bulletin de la Societe Chemique de France, p. 283, 1972) and dodecyltriphenylphosphonium bromide of the formula (XXVIII) (Chemistry and Industry (London), p. 1086, 1958) gives methyl cis- and/or trans-4-alkenylpyrrole-2-carboxylate of the formula (XXIX). Further, the carboxylate may be hydrolyzed in accordance with a usual method into cis- and/or trans-4-alkenylpyrrole-2-carboxylic acid of the formula (XXX), a compound according to the present invention.

Method 8:

Synthesis of an ester of pyrrole carboxylic acid

Pyrrole carboxylic acid may be esterified according to either of the following methods:

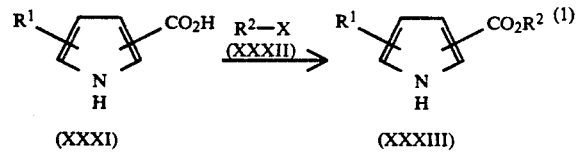

(XXXI)      (XXXIII)

in which $R^1$ and $R^2$ each has the same meaning as described above, provided that $R^2$ is not a phenyl group, and X represents a halogen atom.

An ester of pyrrole carboxylic acid represented by the above formula (XXXIII) may be obtained by reacting pyrrole carboxylic acid of the formula (XXXI) with a halide compound of the formula (XXXII) in an inert solvent such as tetrahydrofuran or dimethylformamide in the presence of a base such as sodium hydride or triethylamine at a temperature of from −10° C. to the boiling point of the solvent.

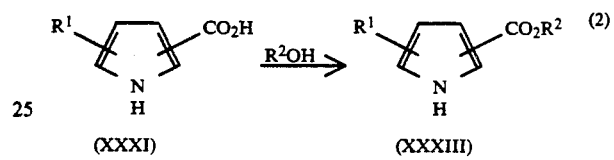

(XXXI)      (XXXIII)

in which $R^1$ and $R^2$ each has the same meaning as defined above.

The pyrrolecarboxylic acid (XXXI) is first converted into a mixed acid anhydride according to a method usually employed at dehydrative condensation, e.g., using ethyl chlorocarbonate and an organic base such as triethylamine, followed by reacting the mixed acid anhydride with an appropriate alcohol or phenol to afford the ester of pyrrolecarboxylic acid represented by the above formula (XXXIII). The ester (XXXIII) was also obtained by reacting the acid (XXXI) with an appropriate alcohol or phenol in the presence of a condensating agent such as dicyclohexylcarbodiimide.

Method 9:

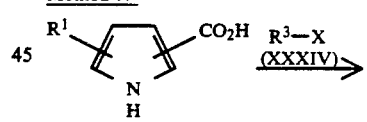

(XXXI)

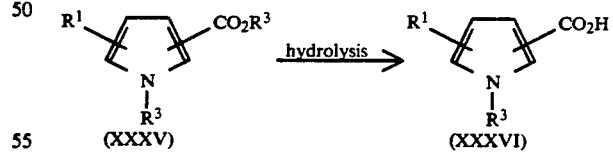

(XXXV)      (XXXVI)

in which $R^1$ and $R^3$ each has the same meaning as described above and X represents a halogen atom.

The pyrrolecarboxylic acid (XXXI) is reacted with an appropriate halide compound (XXXIV) in the presence of a base such as sodium hydride, metal potassium, or sodium ethoxide in an inert solvent such as ether, tetrahydrofuran or dimethylformamide at a temperature of from −10° C. to the boiling point of the solvent. The resultant compound (XXXV) is heated under refulx in an aqueous alkaline solution containing an alcoholic solvent such as ethanol and then hydrolyzed into an pyrrolecarboxylic acid represented by the above formula (XXXVI). An ester of pyrrolecarboxylic acid can be used as the starting material instead of the compound (XXXI).

The compounds according to the present invention is useful as an active ingredient of a pharmaceutical composition for treating hyperlipemia and/or arterioclerosis. The pharmaceutical composition comprises a therapeutically effective amount of a pyrrolecarboxylic acid derivative or salt thereof as defined hereinbefore, in admixture with a pharmaceutically acceptable carrier or diluent. The composition may be administrated, preferably, orally to a patient, and the formulation for the oral administration may be tablet, granule, powder, capsule, etc. The pharmaceutical composition may further include usual additives known in the art, for example, an excipient, such as glucose, lactose, corn starch or mannitol, a binder such as hydrozypropyl cellulose (HPC) and carboxymethyl cellulose (CMC), a disintegrating agent such as starch or powdery gelatin, a lubricating agent such as talc or magnesium stearate, etc.

The dose of the compound according to the present invention, in the case of oral administration, is from 10 mg to 10 g, preferably, from 100 mg to 5 g per day for an adult, which may be administrated all at once or divisionally for 2-3 times.

EXAMPLES

The present invention is further illustrated in detail with reference to the following examples. It should be understood that the present invention is not limited solely to these examples. Synthetic Examples 1-11 show the synthesis of starting materials and the intermediates in the course of preparing the compounds according to the invention, while Examples 1-86 show the synthesis of the compounds according to the invention.

SYNTHETIC EXAMPLE 1

Preparation of 2-tetradecanoylpyrrole

To 30 ml (90 mmol) of an ethereal solution of 3M methylmagnesium bromide was added 6.04 g (90 mmol) of pyrrole at room temperature under stirring, and then the mixture was heated under reflux for 30 minutes. After cooling the reaction mixture with ice, myristoyl chloride which was obtained from 9.14 g (40 mmol) of myristic acid by an ordinary procedure was added dropwise thereto. The whole was then heated under reflux for 1 hour and cooled to room temperature. The resulting mixture was poured into ice-water containing ammonium chloride and extracted with ethyl acetate. The extract was washed with water and dried over anhydrous magnesium sulfate. After removing the solvent under reduced pressure, the residue was purified by subjecting it to column chromatography (eluent: ethyl acetate/hexane=1/5) to obtain 7.31 g (66% yield) of 2-tetradecanoylpyrrole.

IR (KBr) cm$^{-1}$: 3310, 2940, 1645.

NMR (CDCl$_3$) δ: 0.88 (3H, t), 1.25 (20H, m), 1.71 (2H, m), 2.75 (2H, t), 6.28 (1H, m), 6.90 (1H, m), 7.01 (1H, m).

SYNTHETIC EXAMPLE 2

Preparation of 2-tetradecylpyrrole

A mixture of 7.31 g (26 mmol) of 2-tetradecanoylpyrrole obtained in Synthetic Example 1, 30 ml (610 mmol) of 100% hydrazine hydrate and 20 g (350 mmol) of potassium hydroxide was heated at 200° C. for 3 hours in 200 ml of diethylene glycol and cooled to room temperature. The resulting mixture was diluted with water and extracted with ether. The extract was washed with water and dried over anhydrous magnesium sulfate. After removing the solvent, the residue was purified by subjecting it to column chromatography (eluent: ethyl acetate/hexane=1/10) to obtain 6.14 g (88% yield) of 2-tetradecylpyrrole.

IR (KBr) cm$^{-1}$: 3380, 2940.

NMR (CDCl$_3$) δ: 0.89 (3H, t), 1,27 (22H, m), 1.63 (2H, m), 2.61 (2H, t), 5.92 (1H, m), 6.14 (1H, m), 6.68 (1H, m), 7.90 (1H, broad s).

Example 1

Preparation of ethyl 5-tetradecylpyrrole-2-carboxylate (Compound No.41 in Table 1)

Into 20 ml of anhydrous ether was dissolved 4.00 g (15 mmol) of 2-tetradecylpyrrole obtained in Synthetic Example 2, and then 7 ml (21 mmol) of ca. 3M ethereal solution of methylmagnesium bromide was added thereto at room temerature. The resulting mixture was heated under reflux for 30 minutes. Under cooling with ice water, 2 ml (21 mmol) of ethyl chlorocarbonate was added to the mixture. After heating under reflux for 10 hours, the resulting mixture was cooled to room temperature, poured into ice water containing ammonium chloride, and extracted with ethyl acetate. The extract was washed with water and dried over anhydrous megnesium sulfate. After removing the solvent under reduced pressure, the residue was purified by subjecting it to column chromatography (eluent: ethyl acetate/hexane=1/10) to obtain 1.89 g (37% yield) of ethyl 5-tetradecylpyrrole-2-carboxylate, m.p. 60°-63° C.

IR (KBr) cm$^{-1}$: 3310, 2930, 1675.

NMR (CDCl$_3$) δ: 0.88 (3H, t), 1,26 (22H, m), 1.34 (3H, m), 1.59 (2H, m), 2.60 (2H, t), 4.28 (2H, q), 5.97 (1H, m), 6.83 (1H, m), 8.75 (1H, broad s).

EXAMPLE 2

Preparation of 5-tetradecylpyrrole-2-carboxylic acid (Compound No.40 in Table 1)

Ethyl 5-tetradecylpyrrole-2-carboxylate obtained in Example 1 (0.50 g, 1.5 mmol) was dissolved in 20 ml of ethanol followed by adding 3 ml (3 mmol) of aqueous 1N sodium hydroxide solution thereto. The resulting mixture was heated under reflux for 6 hours. After cooling the mixture, precipitates were filtered, washed well with ether, suspended in diluted hydrochloric acid, and extracted with ether. The extract was further washed with an aqueous saturated solution of sodium chloride and dried over anhydrous megnesium sulfate. A removal of the solvent under reduced pressure afforded 0.34 g (74% yield) of 5-tetradecylpyrrole-2-carboxylic acid, m.p. 68°-69° C.

IR (KBr) cm$^{-1}$: 3340, 3255, 2930, 1660, 1500.

NMR (CDCl$_3$) δ: 0.88 (3H, t), 1,26 (22H, m), 1.64 (2H, m), 2.62 (2H, t), 6.02 (1H, m), 6.97 (1H, m). 8.90 (1H, broad s).

SYNTHETIC EXAMPLE 3

Preparation of ethyl γ-ketooctadecanoate ethylene ketal

A mixture of 9.25 g (28 mmol) of ethyl γ-ketooctadecanoate and 9.00 g of ethylene glycol (145 mmol) was refluxed for 5 hours in 300 ml of toluene in the presence of a small amount of p-toluenesulfonic acid catalyst while removing water by means of Dean-Stark apparatus. The resulting mixture was washed with an aqueous saturated sodium bicarbonate solution and then with an aqueous saturated solution of sodium chloride. An oily product obtained by removing the solvent under reduced pressure was subjected to column chromatography over silica gel (eluent: ethyl acetate/hexane=1/10) to give 7.42 g (71% yield) of ethyl γ-ketooctadecanoate ethylene ketal.

IR (Neat) cm$^{-1}$: 2290, 1740.

NMR (CDCl$_3$) δ: 0.88 (3H, t), 1.25 (24H, m), 1.25 (3H, t), 1.60 (2H, m), 1.98 (2H, t), 2.36 (2H, t), 3.93 (4H, s), 4.10 (2H, q).

EXAMPLE 3

Preparation of ethyl 5-tetradecylpyrrole-3-carboxylate (Compound No.42 in Table 1)

To 20 ml of an ethereal suspension of 1.20 g (30 mmol) of 60% sodium hydride was added dropwise 20 ml of an ethereal solution of 7.42 g (20 mmol) of ethyl γ-ketooctadecanoate ethylene ketal prepared in Synthetic Example 3 and 1.93 g (26 mmol) of ethyl formate under stirring at room temperature. The mixture was stirred at room temperature for 18 hours. Then, 0.70 g (17 mmol) of 60% sodium hydride and 1.00 g (13 mmol) of ethyl formate were further added to the mixture and the whole was stirred at the room temperature for 50 hours. The reaction was terminated by adding diluted hydrochloric acid and the resulting mixture was extracted with ether. A residue obtained by removing the solvent from the extract under reduced pressure was treated with 30 ml of concentrated hydrochloric acid under vigorous stirring for 1.5 hours. The resulting mixture was extracted with ether, washed with a saturated sodium chloride solution and dried over anhydrous magnesium sulfate. After removing the solvent under a reduced pressure, the residue was purified by subjecting it to column chromatography over silica gel (eluent: ethyl acetate/hexane=1/10) to obtain 3.63 g (51% yield) of ethyl γ-keto-α-formyloctadecanoate.

To 4.13 g (12 mmol) of the resulting ethyl γ-keto-α-formyloctadecanoate was added 150 ml of an ammonia-saturated ethanol solution and the mixture was then heated under reflux for 14 hours. After removing the solvent under reduced pressure, the residue was purified by subjecting it to silica gel column chromatography (eluent: ethyl acetate/hexane=1/10) to obtain 3.53 g (90% yield) of ethyl 5-tetradecylpyrrole-3-carboxylate, m.p. 59°-62° C.

IR (KBr) cm$^{-1}$: 3320, 2940, 1680.

NMR (CDCl$_3$) δ: 0.88 (3H, t), 1.23 (22H, m), 1.33 (3H, t), 1.60 (2H, m), 2.56 (2H, t), 4.26 (2H, q), 6.30 (1H, m), 7.29 (1H, m), 8.20 (1H, broad s).

EXAMPLE 4

Preparation of 5-tetradecylpyrrole-3-carboxylic acid (Compound No. 38 in Table 1)

An aqeous solution of 1N sodium hydroxide (25 ml) was added to an ethanol solution (120 ml) of 3.53 g (11 mmol) of ethyl 5-tetradecylpyrrole-3-carboxylate, and the whole was heated under reflux for 16 hours. After removal of the ethanol, the residue was acidified with diluted hydrochloric acid and extracted with ethyl acetate. The extract was then washed with water and dried over anhydous magnesium sulfate. The residue was purified by subjecting it to silica gel column chromatography (eluent: ethyl acetate/hexane=1) to obtain 2.19 g (68% yield) of 5-tetradecylpyrrole-3-carboxylic acid, m.p. 83°-85° C.

IR (KBr) cm$^{-1}$: 3470, 2950, 1670.

NMR (CDCl$_3$) δ: 0.88 (3H, m), 1.25 (22H, m), 1.61 (2H, m), 2.57 (2H, t), 6.36 (1H, m), 7.38 (1H, m), 8.20 (1H, broad s).

SYNTHETIC EXAMPLE 4

Preparation of ethyl 5-tridecanoylpyrrole-3-carboxylate

To a solution (20 ml) of 2.78 g (20 mmol) of ethyl pyrrole-3-carboxylate in benzene was added tridecanoyl chloride prepared from 4.28 g (20 mml) of tridecanoic acid in a conventional manner, followed by further dropwise addition of 3.5 ml (30 mmol) of stannic chloride. After the addition, the mixture was stirred for 15 hours at room temperature, treated with diluted hydrochloric acid and extracted with ethyl acetate. The extract was washed with water and dried over anhydrous magnesium sulfate. After removing the solvent under reduced pressure, the residue was purified by subjecting it to silica gel column chromatography (eluent: ethyl acetate/hexane=1/7) to obtain 4.85 g (72% yield) of ethyl 5-tridecanoylpyrrole-3-carboxylate.

IR (KBr) cm$^{-1}$: 3290, 2920, 1700, 1660.

NMR (CDCl$_3$) δ: 0.88 (3H, t), 1.25 (18H, m), 1.25 (3H, t), 1.71 (2H, m), 2.78 (2H, t), 4.25 (1H, q), 7.31 (1H, m), 7.59 (1H, m), 9.60 (1H, broad s).

SYNTHETIC EXAMPLE 5

Preparation of ethyl 5-tridecanoylpyrrole-3-carboxylate dithioethylene ketal

Boron trifluoride-diethyl ether complex (5 ml) was added to a mixture of 4.85 (1.45 mmol) of ethyl 5-tridecanoylpyrrole-3-carboxylate prepared in Synthetic Example 4 and a solution (40 ml) of 5 ml of ethanedithiol in acetic acid. After stirring for 2.5 hours at room temperature, the mixture was treated with water, extracted with ethyl acetate, washed with an aqueous solution of sodium carbonate and an aqueous saturated solution of sodium chloride succesively, and dried over anhydrous magnesium sulfate. The solvent was removed under reduced pressure and the residue was purified by subjecting it to silica gel column chromatography (eluent: ethyl acetate/hexane=1/7) to obtain 3.74 g (63% yield) of ethyl 5-tridecanoylpyrrole-3-carboxylate dithioethylene ketal.

IR (KBr) cm$^{-1}$: 3350, 2910, 1680.

NMR (CDCl$_3$) δ: 0.88 (3H, t), 1.25 (18H, m), 1.61 (2H, m), 2.56 (2H, t), 3.40 (4H, m), 4.23 (2H, q), 6.36 (1H, m), 7.39 (1H, m), 8.28 (1H, broad s).

EXAMPLE 5

Preparation of ethyl 5-tridecylpyrrole-3-carboxylate (Compound No.32 in Table 1)

A mixture of 3.74 g (9.1 mmol) of ethyl 5-tridecanoylpyrrole-3-carboxylate dithioethylene ketal prepared in Sythetic Example 5 and 30 ml of Raney-nickel in 200 ml of ethanol was heated under reflux for 2 hours. After filteration through celite, the separated Raney-nickel was washed well with ethanol. The solvent was removed under reduced pressure, the residue was purified by subjecting it to silica gel column chromatography (eluent: ethyl acetate/hexane=1/7) to obtain 2.60 g (89% yield) of ethyl 5-tridecylpyrrole-3-carboxylate, m.p. 59.5°-60.5° C.

IR (KBr) cm$^{-1}$: 3320, 2930, 1680.

NMR (CDCl$_3$) δ: 0.88 (3H, t), 1.25 (20H, m), 1.60 (2H, m), 2.56 (2H, t), 4.28 (2H, q), 6.31 (1H, m), 7.30 (1H, m), 8.30 (1H, broad m).

EXAMPLE 6

Preparation of 5-tridecylpyrrole-3-carboxylic acid (Compound No.30 in Table 1)

To an ethanol solution (40 ml) of 2.60 g (8.1 mmol) of ethyl 5-tridecylpyrrole-3-carboxylate prepared in Example 5 was added 10 ml of an aqueous solution containing 1.40 g (33 mmol) of sodium hydroxide. The mixture was heated under reflux for 36 hours. After removing the ethanol, the mixture was acidified with hydrochloric acid, extracted with ethyl acetate and dried over anhydrous magnesium sulfate. The solvent was removed under reduced pressure to give crystals, which were purified by subjecting them to column chromatography over silica gel (eluent: ethyl acetate/hexane=¼) to obtain 2.04 g (86% yield) of pure 5-tridecylpyrrole-3-carboxylic acid, m.p. 82°–84° C.

IR (KBr) cm$^{-1}$: 3450, 2920, 1665.

NMR (CDCl$_3$) δ: 0.88 (3H, t), 1.26 (20H, m), 1.61 (2H, m), 2.57 (2H, t), 6.36 (1H, m), 7.39 (1H, m), 8.24 (1H, broad m).

EXAMPLE 7

Preparation of 5-(1-pentadecenyl)pyrrole-3-carboxylic acid (Compound No.76 in Table 1)

Sodium borohydride (500 mg, 13 mmol) was added to an ethanol solution (100 ml) of 4.59 g (13 mmol) of ethyl 5-pentadecanoylpyrrole-3-carboxylate prepared in the same manner as in Synthetic Example 4. The mixture was stirred at room temperature for 16 hours. After a removal of the ethanol under reduced pressure, the mixture was treated with water, extracted with ether, washed with water and dried over anhydrous magnesium sulfate. A removal of the solvent under reduced pressure quantitatively gave an alcoholic compound. To the resulting product were added 3.53 g (63 mmol) of potassium hydroxide in ethanol (35 ml) and water (12 ml), and the mixture was heated under reflux for 5 days. The resulting mixture was acidified with hydrochloric acid and extracted with ethyl acetate. The extract was washed with water and dried over anhydrous magnesium sulfate. After removing the solvent under reduced pressure, the residue was purified by subjecting it to column chromatography over silica gel (eluent: ethyl acetate/hexane=¼) to obtain 2.33 g (60% yield) of 5-(1-pentadecenyl)pyrrole-3-carboxylic acid, m.p. 90°–96° C.

IR (KBr) cm$^{-1}$: 3450, 2940, 1670.

NMR (CDCl$_3$) δ: 0.88 (3H, t), 1.28 (22H, m), 2.17 (2H, m), 5.88 (1H, m), 6.20 (1H, m), 6.53 (1H, m), 7.42 (1H, m), 8.49 (1H, broad s).

EXAMPLE 8

Preparation of 5-tetradecylpyrrole-3-carboxylic acid (Compound No.38 in Table 1)

An ethanol solution (20 ml) of 3.05 g (10 mmol) of 5-(1-tetradecenyl)pyrrole-3-carboxylic acid prepared in the same manner as in Synthetic Example 7 was subjected to catalytic reduction for 2 hours in the presence of 300 mg of 10% palladium black. After removing the solvent the preduct was crystallized from heptane to obtain 2.50 g (82% yield) of a product identical to the one prepared in Example 4.

The melting point, IR and NMR spectra of the product are substantially coincident with those in Example 4.

SYNTHETIC EXAMPLE 6

Preparation of methyl 4-tetradecanoylpyrrole-2-carboxylate

To a solution (5 ml) of 1.25 g (10 mmol) of methyl pyrrole-2-carboxylate in benzene was added 2.71 g (11 mmol) of tetradecanoyl chloride under ice-cooling, followed by adding 1.73 ml (15 mmol) of stannic chloride dropwise thereto. The mixture was stirred for 2 hours at room temperature, treated with diluted hydrochloric acid and extracted with ethyl acetate. The extract was washed with water and dried over anhydrous magnesium sulfate. After removing the solvent under reduced pressure, the product was purified by subjecting it to column chromatography over silica gel (ethyl acetate/hexane=1/7) to obtain 1.80 g (54% yield) of methyl 4-tetradecanoylpyrrole-2-carboxylate.

IR (KBr) cm$^{-1}$: 3290, 2920, 1705, 1665.

NMR (CDCl$_3$) δ: 0.88 (3H, t), 1.30 (20H, m), 1.70 (2H, m), 2.75 (2H, t), 3.88 (3H, s), 7.29 (1H, m), 7.53 (1H, m), 9.30 (1H, broad s).

EXAMPLE 9

Preparation of methyl 4-tetradecylpyrrole-2-carboxylate (Compound No.39 in Table 1)

A solution (30 ml, 90 mmol) of ca. 3M diborane in tetrahydrofuran was added to 1.80 g (5.4 mmol) of methyl 4-tetradecanoylpyrrole-2-carboxylate prepared in Synthetic Example 6, and then 1 ml of boron trifluoride-diethyl ether complex was further added thereto. The mixture was allowed to stand overnight at room temperature. Methanol and water were successively added to the reaction mixture, and the resulting mixture was extracted with ethyl acetate. The extract was washed with water and dried over anhydrous magnesium sulfate. After removing the solvent under reduced pressure, the residue was purified by subjecting it to column chromatography over silica gel (eluent: ethyl acetate/hexane=¼) to obtain 0.22 g (13% yield) of methyl 4-tetradecylpyrrole-2-carboxylate, m.p. 80°–82° C.

IR (KBr) cm$^{-1}$: 3360, 2950, 1695.

NMR (CDCl$_3$) δ: 0.88 (3H, t), 1.25 (22H, m), 1.56 (2H, m), 2.45 (2H, t), 3.83 (3H, s), 6.74 (2H, m) 8.85 (1H, broad s).

EXAMPLE 10

Preparation of 4-tetradecylpyrrole-2-carboxylic acid (Compound No.37 in Table 1)

A solution (1 ml) of 2N sodium hydroxide was added to an ethanol solution (5 ml) of 0.22 g (0.69 mmol) of methyl 4-tetradecylpyrrole-2-carboxylate prepared in Example 9 and heated under reflux for 13 hours. Water was added to the resulting mixture, and then washed with ether. After acidifying the aqueous layer with hydrochloric acid, the mixture was extracted with ether and dried over anhydrous magnesium sulfate. The removal of the solvent afforded 0.19 g (95% yield) of 4-tetradecylpyrrole-2-carboxylic acid, m.p. 148°–150° C.

IR (KBr) cm$^{-1}$: 3400, 2930, 1690.

NMR (CDCl₃) δ: 0.88 (3H, t), 1.25 (22H, m), 1.53 (2H, t), 6.94 (1H, m), 6.97 (1H, m), 9.10 (1H, broad s).

EXAMPLES 11 to 32

In line with the procedures described in the above Examples and/or the following procedures, compounds in Table 2 were prepared.

Method (I)

Preparation of propyl 5-tridecylpyrrole-3-carboxylate

To 25 ml of tetrahydrofuran were added 1.50 g (5.11 mmol) of 5-tridecylpyrrole-3-carboxylic acid and 1.27 g (6.15 mmol) of dicyclohexylcarbodiimide, followed by adding 3.8 ml of n-propyl alcohol and 62 mg of dimethylaminopyridine. Then the mixture was heated at 60° C. for 10 hours under stirring. After cooling, the resulting precipitates were filtered off and washed well with ether. The filtrate and the washing liquid were combined and concentrated. The residue was purified by subjecting it to column chromatography over silica gel (eluent: ethyl acetate/hexane=1/20) to obtain 1.26 g (73% yield) of propyl 5-tridecylpyrrole-3-carboxylate, m.p. 51°-52° C.

IR (KBr) cm⁻¹: 3280, 2930, 1675.

NMR (CDCl₃) δ: 0.88 (3H, t), 0.97 (3H, t), 1.25 (20H, m), 1.65 (4H, m), 2.54 (2H, t), 4.17 (2H, t), 6.31 (1H, m), 7.28 (1H, m), 9.04 (1H, broad s).

Method (II)

Preparation of 2-bromoethyl 5-tridecylpyrrole-3-carboxylate

To a solution (20 ml) of 1.47 g (5.0 mmol) of 5-tridecylpyrrole-3-carboxylic acid in tetrahydrofuran were added 0.60 g (5.53 mmol) of ethyl chlorocarbonate and 0.60 g (5.94 mmol) of triethylamine, and the whole was stirred at room temperature for 10 minutes. After adding 1.88 g (15 mmol) of 2-bromoethanol, the mixture was heated under reflux for 1.5 hours. After further addition of 0.94 (7.5 mmol) of 2-bromoethanol, the mixture was heated under reflux for 9 hours. The resulting mixture was cooled, acidified with a diluted hydrochloric acid and extracted with ethyl acetate. The extract was washed with water and dried over magnesium sulfate. A removal of the solvent under reduced pressure afforded an oily product, which was purified by subjecting it to column chromatography over silica gel (eluent: ethyl acetate/hexane=1/10) to obtain 1.05 g (53% yield) of 2-bromoethyl 5-tridecylpyrrole-3-carboxylate, m.p. 67°-69.5° C.

IR (KBr) cm⁻¹: 3340, 2930, 1690.

NMR (CDCl₃) δ: 0.88 (3H, t), 1.33 (20H, m), 1.60 (2H, m), 2.56 (2H, t), 3.59 (1H, t), 3.76 (1H, t), 4.49 (2H, m), 6.34 (1H, m), 7.34 (1H, m), 8.20 (1H, broad s).

TABLE 2

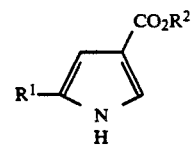

| Example No. | R¹ | R² | M.P. (°C.) |
|---|---|---|---|
| 11 | $CH_3(CH_2)_7-$ | H | 77–18 |
| 12 | $CH_3(CH_2)_9-$ | " | 72–77 |
| 13 | $CH_3(CH_2)_{10}-$ | " | 76–78.5 |
| 14 | $CH_3(CH_2)_{11}-$ | " | 74–75 |
| 15 | $CH_3(CH_2)_{14}-$ | " | 86–89 |
| 16 | $CH_3(CH_2)_{15}-$ | " | 87–89 |
| 17 | $CH_3(CH_2)_{16}-$ | " | 90–92 |
| 18 | $CH_3(CH_2)_{17}-$ | " | 92–94 |
| 19 | $CH_3(CH_2)_{18}-$ | " | 93–95 |
| 20 | $CH_3(CH_2)_{19}-$ | " | 97–98 |
| 21 | $CH_3(CH_2)_9CH=CH-$ | " | 72–76 |
| 22 | $CH_3(CH_2)_{10}CH=CH-$ | " | 87–93 |
| 23 | $CH_3(CH_2)_{11}CH=CH-$ | " | 73–80 |
| 24 | $CH_3(CH_2)_{14}CH=CH-$ | " | 84–92 |
| 25 | $CH_3(CH_2)_{12}-$ | $-CH_3$ | 57–58 |
| 26 | " | $-C_3H_7$ | 51–52 |
| 27 | " | $-C_4H_9$ | 36–37 |
| 28 | " | $-CH_2SCH_3$ | 60–61.5 |
| 29 | " | $-CH_2CH_2Br$ | 67–69.5 |
| 30 | " | $-CH_2CH_2N(CH_3)_2 \cdot HCl$ | 167–168 |
| 31 | " | $-CH_2CH(OH)CH_2OH$ | 109–110 |
| 32 | " | $-C_6H_5$ | 91.5–93.5 |

SYNTHETIC EXAMPLE 7

Preparation of methyl 4-tridecanoylpyrrole-2-carboxylate

Tridecanoic acid (102.8 g, 0.48 mol) was dissolved into 480 ml of methylene chloride, and 52.6 ml (0.72 mol) of thionyl chloride and 0.2 ml of N,N-dimethylformamide were added thereto. The mixture was allowed to stand overnight followed by concentration under reduced pressure, and the remaining oil was added to 400 ml of methylene chloride containing 106.6 g (0.8 mol) of anhydrous aluminium chloride. A solution of 50.05 g (0.4 mol) of methyl pyrrole-2-carboxylate in 200 ml of methylene chloride was added dropwise to the mixture for ca. 40 minutes at 3° to 9° C. After the addition was finished, the temperature was raised gradually to room temperature, and the mixture was stirred for 2 hours followed by pouring it into 800 ml of ice water. To this mixture was added 1000 ml of methylene chloride to completely dissolve the crystals. The organic layer was separated, washed with water three times and dried over anhydrous magnesium sulfate. After concentration under reduced pressure, the residue was recrystallized from 400 ml of ethyl acetate and 400 ml of hexane to give 107.2 g (83% yield) of methyl 4-tridecanoylpyrrole-2-carboxylate as white crystals, m.p. 92°-93° C.

IR (KBr) cm⁻¹: 3270, 2920, 2855, 1690, 1660, 1565, 1455, 1385, 1290, 1215.

¹H NMR (CDCl₃, 250 MHz) δ: 0.88 (3H, t, J=6.6 Hz), 1.15–1.38 (18H, m), 1.65–1.75 (2H, m), 2.75 (2H, t, J=7.5 Hz), 3.89 (3H, s), 7.28–7.30 (1H, m), 7.53–7.55 (1H, m), 9.52 (1H, broad s).

SYNTHETIC EXAMPLE 8

Preparation of methyl 4-tridecanoylpyrrole-2-carboxylate dithioethylene ketal

To 18.29 g (56.9 mmol) of methyl 4-tridecanoylpyrrole-2-carboxylate prepared in Synthetic Example 7 dissolved in 140 ml of acetic acid were added 14.0 ml (167 mmol) of 1,2-ethanedithiol and 14 ml of boron trifluoride-diethyl ether complex, and the whole was stirred overnight under ice-cooling. After concentrating the reaction mixture under reduced pressure, 100 ml of water was added to the residue and the mixture was extracted with 200 ml (100 ml×2) of ethyl acetate. The two extracts were combined, washed with a 5% aqueous solution of sodium hydroxide and then with a saturated solution of sodium chloride, dried over anhydrous magnesium sulfate and concentrated under reduced pressure. The residue was recrystallized from a mixed solvent of acetic acid and hexane to give methyl 4-tridecanoylpyrrole-2-carboxylate dithioethylene ketal. The mother liquor was then subjected to column chromatography over silica gel (eluent: ethyl acetate/hexane=1/6) to separate the desired product which remained in the recrystallization solvent. Total amount obtained: 15.44 g (68% yield), m.p.: 77°-78° C.

IR (KBr) cm$^{-1}$: 3360, 2940, 2860, 1705, 1440, 1385, 1265, 1210, 1120.

$^1$H NMR (CDCl$_3$, 250 MHz) δ: 0.88 (3H, t, J=6.6 Hz), 1.20-1.40 (20H, m), 2.22-2.28 (2H, m), 3.25-3.41 (4H, m) 3.84 (3H, s), 6.92 (1H, s), 7.05-7.07 (1H, m), 9.08 (1H. broad s).

EXAMPLE 33

Preparation of methyl 4-tridecylpyrrole-2-carboxylate (Compound No.15 in Table 1)

Methyl 4-tridecanoylpyrrole-2-carboxylate dithioethylene ketal (15.06 g, 37.9 mmol) prepared in Synthetic Example 8 was added to a mixed solution of 750 ml of ethanol and 150 ml of Raney-nickel (activated type, manufactured by Aldrich Co.) which was washed with water and ethanol successively. The mixture was heated under reflux for 30 minutes. After cooling it to ca. 30° C., the Raney-nickel was filtered off and the filtrate was concentrated under reduced pressure. Recrystallization of the residue from ethanol gave 10.70 g (91.8% yield) of methyl 4-tridecylpyrrole-2-carboxylate as white crystals, m.p. 80°-82° C.

IR (KBr) cm$^{-1}$: 3340, 2920, 2850, 1690, 1445, 1390, 1265, 1205, 1130.

$^1$H NMR (CDCl$_3$, 250 MHz) δ: 0.88 (3H, t, J=6.6 Hz), 1.2-1.4 (20H, m), 1.49-1.62 (2H, m), 2.45 (2H, t, J=7.6 Hz), 3.83 (3H, s), 6.72-6.75 (2H, m), 8.88 (1H, broad s).

EXAMPLE 34

Preparation of 4-tridecylpyrrole-2-carboxylic acid (Compound No.14 in Table 1)

To 10.01 g (32.6 mmol) of methyl 4-tridecylpyrrole-2-carboxylate prepared in Example 32 were added 200 ml of ethanol, 80 ml of water and 5.5 g (131 mmol) of 95% sodium hydroxide and the resulting mixture was heated under reflux for 1 hour. After cooling, 100 ml of water was added thereto. The resulting mixture was acidified with hydrochloric acid and extracted with a mixed solvent of 400 ml of ethyl ether, 100 ml of ethyl acetate and 300 ml of tetrahydrofuran. An aqueous layer was extracted again with 100 ml of ethyl acetate. Then both extracts were combined, washed with a saturated solution of sodium chloride and dried over anhydrous magnesium sulfate. After concentrating the resulting solution under reduced pressure, the recrystallization of the product from a mixed solvent of hexane and tetrahydrofuran gave 7.55 g of 4-tridecylpyrrole-2-carboxylic acid as white crystals, m.p. 150°-151° C.

IR (KBr) cm$^{-1}$: 3390, 2960, 2925, 2860, 1685, 1495, 1440, 1280, 1130, 1120.

$^1$H NMR (DMSO—d$_6$, 250 MHz) δ: 0.84 (3H, t, J=6.5 Hz), 1.22 (20H, broad s), 1.40-1.52 (2H, m), 2.35 (2H, t, J=7.4 Hz), 6.53 (1H, s), 6.71 (1H, s).

SYNTHETIC EXAMPLE 9

Preparation of methyl 4-dodecanoylpyrrole-2-carboxylate

Following the procedures of Synthetic Example 7 and using 213 g (1.06 mol) of lauric acid as a starting material, there was obtained 245.5 g (90% yield) of methyl 4-dodecanoylpyrrole-2-carboxylate, m.p. 102°-103° C.

IR (KBr) cm$^{-1}$: 3270, 2920, 2850, 1690, 1660.

NMR (CDCl$_3$) δ: 0.88 (3H, t), 1.25 (16H, m), 1.70 (2H, m), 2.75 (2H, t), 3.88 (3H, s), 7.30 (1H, m), 7.53 (1H, m), 9.50 (1H, broad s).

SYNTHETIC EXAMPLE 10

Preparation of methyl 4-(1-hydroxydodecyl)pyrrole-2-carboxylate

To 245.5 g (0.80 mol) of methyl 4-dodecanoypyrrole-2-carboxylate prepared in Synthetic Example 9 were added 1.5 liters of tetrahydrofuran and 0.15 liters of methanol. Under stirring at 10°-21° C., 15.1 g (0.40 mol) of sodium borohydride was added portionwise thereto. After stirring at 20° C. for 1 hour, 7.5 g (0.20 mmol) of sodium borohydride was further added. The mixture was stirred at 20° C. for 1 hour. After removing the solvent under a reduced pressure, the residue was diluted with 700 ml of water and 2.4 liters of ethyl acetate. The organic layer was separated, washed with 700 ml of water and 700 ml of a saturated solution of sodium chloride successively, and finally dried over anhyrous magnesium sulfate. A concentration of the organic layer under reduced pressure gave 247.0 g of light brown crystals. Yield: 99%.

IR (KBr) cm$^{-1}$: 3450, 3240, 2930, 1680.

NMR (CDCl$_3$) δ: 0.88 (3H, t), 1.25 (18H, m), 1.73 (2H, m), 3.85 (3H, s), 4.63 (1H, m), 6.88 (1H, m), 6.92 (1H, m). 9.05 (1H, broad s).

SYNTHETIC EXAMPLE 11

Preparation of methyl 4-(1-acetoxydodecyl)pyrrole-2-carboxylate

To a toluene solution (1.6 liters) of 247.0 g (0.80 mol) of methyl 4-(1-hydroxydodecyl)pyrrole-2-carboxylate prepared in Synthetic Example 10 were added 180 ml (1.91 mol) of acetic anhydride and 180 ml (2.23 mol) of pyridine. The mixture was heated at 105° C. for 2.5 hours, cooled to room temperature, and washed twice with 700 ml of 2N hydrochloric acid. After adding 1.2 liters of a saturated solution of sodium bicarbonate, the whole was stirred at room temperature for 30 minutes. The organic layer was separated, washed sequentially with an aqueous saturated solution of sodium bicarbonate and a saturated solution of sodium chloride (each 700 ml) and dried over anhydrous magnesium sulfate.

The solvent was removed to give crystals, which were then recrystallized from 700 ml of hexane to yield 258.0 g (92% yield) of light brown crystals, m.p. 69°-70° C.

IR (KBr) cm$^{-1}$: 3300, 2920, 1705.

NMR (CDCl$_3$) δ: 0.88 (3H, t), 1.25 (18H, m), 1.86 (2H, m), 2.03 (3H, s), 3.85 (3H, s), 5.73 (1H, t), 6.89 (1H, m), 6.95 (1H, m), 9.08 (1H, broad s).

EXAMPLE 35

Preparation of methyl 4-dodecylpyrrole-2-carboxylate (Compound No.11 in Table 1)

To an ethanol solution (2.0 liters) of 258.0 g (0.73 mol) of methyl 4-(1-hydroxydodecyl)pyrrole-2-carboxylate prepared in Synthetic Example 11 was added 16 g of 10% palladium-carbon. A catalytic reduction with hydrogen was carried out at 50° C. under hydrogen atmosphere. After the reaction was completed within 5.5 hours, 1.5 liters of chloroform was added to the reaction mixture. The catalyst was filtered off, and the solvent was removed under a reduced pressure to give crystals. Recrystallization from 950 ml of ethanol afforded 179.6 g (83% yield) of methyl 4-dodecylpyrrole-2-carboxylate as white crystals, m.p. 68°-69° C.

IR (KBr) cm$^{-1}$: 3340, 2920, 1690.

NMR (CDCl$_3$) δ: 0.88 (3H, t), 1.25 (18H, m), 1.54 (2H, m), 2.44 (2H, t), 3.83 (3H, s), 6.74 (2H, m), 8.88 (1H, broad s).

EXAMPLE 36

Preparation of 4-dodecylpyrrole-2-carboxylic acid (Compound No.10 in Table 1)

To 112.0 g (0.38 mol) of methyl 4-dodecylpyrrole-2-carboxylate prepared in Example 35 were added 1.45 liters of ethanol, 1.45 liters of water and 31.0 g (0.74 mol) of 95% sodium hydroxide, and the whole was heated under reflux for 2 hours. At 80° C., 1.45 liters of hot water was added and, at the same temperature, 6N sulfuric acid was added gradually to adjust the reaction solution to pH 2. After cooling the mixture to 45° C., precipitated crystals were filtered and washed with water. The crystals were dissolved in 4 liters of tetrahydrofuran, and the solution was washed twice with 1 liter of a saturated solution of sodium chloride and dried over anhydrous magnesium sulfate. The solvent was removed under reduced pressure to give crystals, which were then recrystallized from a mixed solvent of 600 ml of tetrahydrofurn and 600 ml of hexane to obtain 92.6 g (87% yield) of 4-dodecylpyrrole-2-carboxylic acid as white crystals, m.p. 152°-153° C.

IR (KBr) cm$^{-1}$: 3380, 2920, 1685.

NMR (DMSO—d$_6$) δ: 0.88 (3H, t), 1.22 (18H, m) 1.44 (2H, m), 2.34 (2H, t), 6.52 (1H, m), 6.71 (1H, m).

EXAMPLES 37 to 46

In line with the procedures described in Example 35 and Example 36, compounds in Table 3 were prepared.

TABLE 3

| Example No. | R$^1$ | R$^2$ | M.P. (°C.) |
| --- | --- | --- | --- |
| 37 | CH$_3$(CH$_2$)$_7$— | H | 152-153 |
| 38 | " | —CH$_3$ | 54-55 |
| 39 | CH$_3$(CH$_2$)$_9$— | H | 150-151 |
| 40 | " | —CH$_3$ | 70-72 |
| 41 | CH$_3$(CH$_2$)$_{10}$— | H | 152-153 |
| 42 | " | —CH$_3$ | 71-72 |
| 43 | CH$_3$(CH$_2$)$_{14}$— | H | 150-151 |
| 44 | " | —CH$_3$ | 80-82 |
| 45 | (CH$_3$)$_3$C(CH$_2$)$_5$— | H | 157-158 |
| 46 | (CH$_3$)$_3$C(CH$_2$)$_8$— | " | 167-168 |

EXAMPLE 47

Preparation of methyl 4-(1-cis-tridecenyl)pyrrole-2-carboxylate (Compound No.73 in Table 1)

A ca. 15% solution (18.5 ml) of n-butyllithium in hexane was added dropwise at −50° C. to a tetrahydrofuran suspension (95 ml) of 16.0 g (31.4 mmol) of dodecyltriphenylphosphonium bromide described in Chemistry and Industry (London) p. 1086, 1958. The temperature was raised to room temperature and the mixture was stirred for 30 minutes. The temperature was again lowered to −50° C. To the mixture was added dropwise a tetrahydrofuran solution (50 ml) of 2.4 g (15.7 mmol) of methyl 4-formylpyrrole-2-carboxylate described in Bulletin de la Societe Chimique de France, p. 283, 1972. The mixture was stirred for 1 hour, diluted with water, extracted with ethyl acetate, washed with an aqueous saturated solution of sodium chloride and dried over anhydrous magnesium sulfate. After removing the solvent under reduced pressure, the residue was purified by subjecting it to column chromatography over silica gel (eluent: ethyl acetate/hexane=1/7) to obtain 3.11 g (65% yield) of methyl 4-(1-cis-tridecenyl)-pyrrole-2-carboxylate, m.p. 51°-52° C.

IR (KBr) cm$^{-1}$: 3300, 2930, 1685.

NMR (CDCl$_3$) δ: 0.88 (3H, t), 1.29 (18H, m), 2.29 (2H, m), 3.86 (3H, s), 5.50 (1H, m), 6.17 (1H, m), 6.93 (2H, m).

EXAMPLE 48

Preparation of 4-(1-cis-tridecenyl)pyrrole-2-carboxylic acid (Compound No.72 in Table 1)

An aqueous solution (25 ml) containing 860 mg (20.4 mmol) of 95% sodium hydroxide was added to an ethanol solution (50 ml) of 3.10 g (10.2 mmol) of methyl 4-(1-cis-tridecenyl)pyrrole-2-carboxylate prepared in Example 46, and the whole was heated under reflux for 1 hour. The reaction mixture was acidified with 6N sulfuric acid and extracted with ethyl acetate. The extract was washed with an aqueous saturated solution of sodium chloride, dried over anhydrous magnesium sulfate and treated with activated carbon. After removing the solvent under reduced pressure, the residue was recrystallized from a mixed solvent of hexane and tetrahydrofuran to give 1.33 g (45% yield) of 4-(1-cis-tridecenyl)pyrrole-2-carboxylic acid, m.p. 157°-158° C.

IR (KBr) cm$^{-1}$: 3390, 2940, 1680.

NMR (DMSO—d$_6$) δ: 0.86 (3H, t), 1.22 (18H, m), 2.21 (2H, m), 5.33 (1H, m), 6.18 (1H, d), 6.72 (1H, m), 6.94 (1H, m).

EXAMPLE 49

Preparation of methyl 4-(1-trans-tridecenyl)pyrrole-2-carboxylate (Compound No.73 in Table 1)

To a tetrahydrofuran suspension (200 ml) of 32 g (62.7 mmol) of dodecyltriphenylphosphonium bromide was added dropwise 40 ml of a ca. 15% solution of n-butyllithium in hexane under ice-cooling. After stirring the reaction mixture for 30 minutes, the temperature was dropped to −78° C. A tetrahydrofuran solution (100 ml) of 4.8 g (31.4 mmol) of methyl 4-formylpyrrole-2-carboxylate was then added dropwise. After stirring for 1 hour, 190 ml of ethanol was further added thereto. The reaction mixture was stirred for 1.5 hour at −78° C., and for another 12 hours while the temperature was gradually raised to room temperature. The resulting mixture was diluted with water, extracted with ethyl acetate, washed with aqueous saturated sodium chloride solution and dried over anhydrous magnesium sulfate. After removing he solvent under reduced pressure, the residue was purified by subjecting it to column chromatography (eluent: ethyl acetate/hexane=1/10) and by recrystallizing twice from hexane to obtain 1.30 g (14% yield) of methyl 4-(1-trans-tridecenyl)pyrrole-2-carboxylate, m.p. 65°-67° C.

IR (KBr) cm$^{-1}$: 3350, 2940, 1690.

NMR (CDCl$_3$) δ: 0.88 (3H, t), 1.32 (18H, m), 2.12 (2H, m), 3.85 (3H, t), 5.95 (1H, s), 6.18 (1H, d), 6.83 (1H, m), 6.95 (1H, m).

EXAMPLE 50

Preparation of 4-(1-trans-tridecenyl)pyrrole-2-carboxylic acid (Compound No.72 in Table 1)

An aqueous solution (8 ml) containing 340 mg (8.0 mmol) of 95% sodium hydroxide was added to an ethanol solution (20 ml) of 1.30 g (4.3 mmol) of methyl 4-(1-trans-tridecenyl)pyrrole-2-carboxylate prepared in Example 48, and the whole was heated under reflux for 1 hour. The reaction mixture was acidified with 6N sulfuric acid and extracted with ethyl acetate. The extract was washed with an aqueous saturated solution of sodium chloride, dried over anhydrous magnesium sulfate and treated with activated carbon. After removing the solvent under reduced pressure, the resulting residue was recrystallized from a mixed solution of hexane and tetrahydrofuran to give 940 mg (72% yield) of 4-(1-trans-tridecenyl)pyrrole-2-carboxylic acid, m.p. 161°-163° C.

IR (KBr) cm$^{-1}$: 3400, 2920, 1690.

NMR (DMSO—d$_6$) δ: 0.84 (3H, t), 1.22 (18H, m), 2.07 (2H, m), 5.89 (1H, m), 6.13 (1H, d), 6.81 (1H, m), 6.84 (1H, m).

EXAMPLE 51

Preparation of ethyl 4-tridecylpyrrole-2-carboxylate (Compound No.16 in Table 1)

After washing 140 mg (3.50 mmol) of 60% sodium hydride with hexane, 20 ml of dimethylformamide was added thereto, and then 90 mg (3.38 mmol) of 4-tridecylpyrrole-2-carboxylic acid prepared in Example 2 was further added portionwise under stirring at room temperature. After stirring for 10 minutes, 5.0 g (31.8 mmol) of ethyl idodide was added to the reaction solution followed by heating it at 55° C. for 22 hours. After cooling, an aqueous solution of hydrochloric acid was added to acidify the mixture, and the resulting mixture was then extracted with ethyl acetate, washed with an aquous saturated solution of sodium chloride and dried over anhydrous magnesium sulfate. After removing the solvent under reduced pressure, the residue was purified by subjecting it to column chromatography over silica gel (eluent: ethyl acetate/hexane=1/10) to obtain 600 mg (55% yield) of ethyl 4-tridecylpyrrole-2-carboxylate as white crystals, m.p. 59°-60° C.

IR (KBr) cm$^{-1}$:3340, 2920, 1690.

NMR (CDCl$_3$) δ: 0.88 (3H, t), 1.26 (20H, m), 1.34 (3H, t), 1.55 (2H, m), 2.45 (2H, m), 4.29 (2H, q), 6.72 (1H, m), 6.75 (1H, m), 8.85 (1H, broad s).

EXAMPLE 52

Preparation of dimethylaminoethyl 4-tridecylpyrrole-2-carboxylate hydrochloride (Compound No.33 in Table 1)

Dimethylaminoethyl 4-tridecylpyrrole-2-carboxylate prepared by the same procedure as in Example 51 was dissolved into a mixed solvent of ethanol and ether, and ethanol containing hydrogen chloride was added thereto. Precipitated crystals were filtered and recrystallized from a mixed solution of ethanol and ether to give the target compound in 41% yield, m.p. 109°-111° C.

IR (KBr) cm$^{-1}$: 3200, 2930, 2600, 1710.

NMR (CDCl$_3$) δ: 0.88 (3H, t), 1.25 (20H, m), 1.53 (2H, m), 2.44 (2H, t), 2.92 (6H, s), 3.38 (2H, t), 4.49 (2H, m), 6.85 (2H, m).

EXAMPLE 53

Preparation of N-butylcarbamoylmethyl 4-tridecylpyrrole-2-carboxylate (Compound No.34 in Table 1)

The target compound was prepared by the same procedure as in Example 51 in 36% yield, m.p. 101°-102° C.

IR (KBr) cm$^{-1}$:3350, 2920, 1670, 1650.

NMR (CDCl$_3$) δ: 0.90 (6H, m), 1.26 (22H, m), 1.55 (4H, m), 2.45 (2H, t), 3.33 (2H, t), 4.73 (2H, s), 6.82 (2H, m).

EXAMPLE 54

Preparation of N,N-diethylcarbamoylmethyl 4-tridecylpyrrole-2-carboxylate (Compound No.35 in Table 1)

The target compound was prepared following the same procedure as in Example 51 in 46% yield, m.p. 107°-108° C.

IR (KBr) cm$^{-1}$: 3310, 2950, 1710, 1640.

NMR (CDCl$_3$) δ: 0.85 (3H, t), 1.12 (3H, t), 1.18 (23H, m), 1.69 (2H, m). 2.42 (2H, t), 3.26 (2H, q), 3.40 (2H, q), 4.84 (2H, s), 6.84 (1H, m), 7.24 (1H, m).

EXAMPLE 55

Preparation of N,N-bis(2-hydroxyethyl)carbamoylmethyl 4-tridecylpyrrole-2-carboxylate (Compound No.36 in Table 1)

The target compound was prepared by the same procedure as in Example 51 in 14% yield, m.p. 99.5°-101° C.

IR (KBr) cm$^{-1}$: 3330, 2940, 1710, 1640.

NMR (CDCl$_3$) δ: 0.88 (3H, t), 1.25 (20H, m), 1.69 (2H, m), 2.43 (2H, t), 3.47 (2H, t), 3.56 (2H, t), 3.84 (4H, m), 6.71 (1H, m), 6.85 (1H, m).

EXAMPLE 56

Preparation of ethyl 1-tetradecylpyrrole-3-carboxylate (Compound No.93 in Table 1)

To dry dimethylformamide (DMF) (15 ml) was added 0.84 g (21 mmol) of sodium hydride (60% oil dispersion), and then 2.78 g (20 mmol) of ethyl pyrrole-3-carboxylate was added portionwise thereto under ice-cooling. After stirring at room temperature for 10 minutes, 6.65 g (24 mmol) of bromotetradecane was added dropwise under ice-cooling. The mixture was stirred for 3.5 hours at room temperature, and then 30 ml of water was added thereto. The resulting mixture was extracted with 70 ml of ethyl acetate, washed with an aqueous solution of sodium chloride and dried over anhydrous magnesium sulfate. After removing the solvent, the remaining oil was purified by subjecting it to column chromatography over silica gel (eluent: ethyl acetate/hexane=1/20–1/10) to obtain 6.33 g (89.0% yield) of ethyl 1-tetradecylpyrrole-3-carboxylate as white crystals, m.p. 32°–33° C.

IR (KBr) cm$^{-1}$: 2940, 2860, 1700, 1540.

NMR (CDCl$_3$) δ: 0.88 (3H, t), 1.25 (22H, m), 1.35 (3H, t), 1.77 (2H, m), 3.85 (2H, t), 4.26 (2H, q), 6.55 (2H, m), 7.27 (1H, m).

EXAMPLE 57

Preparation of 1-tetradecylpyrrole-3-carboxylic acid (Compound No.92 in Table 1)

To a solution of 2.58 g (61.3 mmol) of 95% sodium hydroxide in 100 ml of ethanol and 40 ml of water was added 5.43 g (15.3 mmol) of ethyl 1-tetradecylpyrrole-3-carboxylate obtained in Example 56. After the mixture was heated under reflux for 5 hours, the ethanol was removed under reduced pressure and 100 ml of water was added thereto. Then the mixture was acidified with concentrated hydrochloric acid to precipitate crystals, which were extracted with 70 ml and with 50 ml of ethyl acetate. The extract was washed with an aqueous saturated sodium chloride solution and dried over anhydrous magnesium sulfate. After removing the solvent under reduced pressure, the remaining crystals were recrystallized from hexane to give 3.76 g (79.9% yield) of 1-tetradecylpyrrole-3-carboxylic acid as white crystals, m.p. 66°–67° C.

IR (KBr) cm$^{-1}$: 2930, 2860, 1650, 1545.

NMR (CDCl$_3$) δ: 0.88 (3H, t), 1.25 (22H, m), 1.74 (2H, m), 3.86 (2H, t), 6.60 (2H, m), 7.36 (1H, m).

EXAMPLES 58 to 81

In line with the procedures of Example 55, 56 or 57, compounds in Table 4 were prepared.

TABLE 4

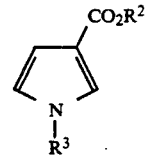

| Example No. | R$^2$ | R$^3$ | M.P. (°C.) |
|---|---|---|---|
| 58 | —C$_2$H$_5$ | CH$_3$(CH$_2$)$_7$— | oil |
| 59 | " | CH$_3$(CH$_2$)$_8$— | " |
| 60 | " | CH$_3$(CH$_2$)$_9$— | " |
| 61 | " | CH$_3$(CH$_2$)$_{10}$— | " |
| 62 | " | CH$_3$(CH$_2$)$_{11}$— | " |
| 63 | " | CH$_3$(CH$_2$)$_{12}$— | " |
| 64 | " | CH$_3$(CH$_2$)$_{14}$— | 38–39 |
| 65 | " | CH$_3$(CH$_2$)$_{15}$— | 40–41 |
| 66 | " | CH$_3$(CH$_2$)$_{16}$— | 48–49 |
| 67 | " | CH$_3$(CH$_2$)$_{17}$— | 46–47 |
| 68 | " | CH$_3$CH$_2$CH=CH(CH$_2$)$_{10}$— | oil |
| 69 | " | CH$_3$(CH$_2$)$_3$CH=CH(CH$_2$)$_{10}$— | " |
| 70 | H | CH$_3$(CH$_2$)$_7$— | 71–72 |
| 71 | " | CH$_3$(CH$_2$)$_8$— | 48–49 |
| 72 | " | CH$_3$(CH$_2$)$_9$— | 60–61 |
| 73 | " | CH$_3$(CH$_2$)$_{10}$— | 60–61 |
| 74 | H | CH$_3$(CH$_2$)$_{11}$— | 65–66 |
| 75 | " | CH$_3$(CH$_2$)$_{12}$— | 69–70 |
| 76 | " | CH$_3$(CH$_2$)$_{14}$— | 75–76 |
| 77 | " | CH$_3$(CH$_2$)$_{15}$— | 73–74 |
| 78 | " | CH$_3$(CH$_2$)$_{16}$— | 79–80 |
| 79 | " | CH$_3$(CH$_2$)$_{17}$— | 78–79 |
| 80 | " | CH$_3$CH$_2$CH=CH(CH$_2$)$_{10}$— | oil |
| 81 | " | CH$_3$(CH$_2$)$_3$CH=CH(CH$_2$)$_{10}$— | " |

EXAMPLE 82

Preparation of 1-hexyl-5-tridecylpyrrole-3-carboxylic acid (Compound No.114 in Table 1)

After washing with hexane, 360 mg (9.0 mmol) of 60% sodium hydride in oil was added to a mixed solution of 8 ml of dimethylformamide and 2 ml of dimethyl sulfoxide, and the whole was stirred at room temperature for 1 hour. To the reaction solution was added 1.50 g (9.1 mmol) of hexyl bromide. After stirred at room temperature for 48 hours, the mixture was acidified with a diluted hydrochloric acid, extracted with ethyl acetate and washed with water. The solvent was removed under reduced pressure, and 20 ml of ethanol, 10 ml of water and 1.0 g of potassium hydroxide were added to the residue. The mixture was heated under reflux for 24 hours, cooled, acidified with hydrochloric acid and extracted with ethyl acetate. The organic layer was separated, washed with water and dried over anhydrous magnesium sulfate. After removing the solvent, the residue was purified by subjecting it to column chromatography over silica gel (eluent: chloroform containing 5% methanol) to obtain 1.20 g (78% yield) of the pure target compound, m.p. 44°–46° C.

IR (KBr) cm$^{-1}$: 2940, 1660.

NMR (CDCl$_3$) δ: 0.88 (6H, m), 1.29 (26H, m), 1.66 (4H, m), 2.47 (2H, t), 3.78 (2H, t), 6.34 (1H, d), 7.29 (1H, d).

EXAMPLE 83 to 86

In line with the procedure described in Example 82, compounds in Table 5 were prepared.

TABLE 5

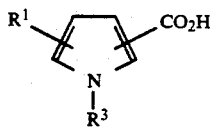

| Example No. | Position of $R^1$ | $R^1$ | $R^3$ | Position of $-CO_2H$ | M.P. (°C.) |
|---|---|---|---|---|---|
| 83 | 5 | $CH_3(CH_2)_{12}-$ | $CH_3(CH_2)_6-$ | 3 | 31–34 |
| 84 | 5 | " | $CH_3(CH_2)_8-$ | 3 | 42–44 |
| 85 | 5 | " | $CH_3(CH_2)_{13}-$ | 3 | 66–67.5 |
| 86 | 4 | " | $CH_3(CH_2)_4-$ | 2 | 35.5–37 |

TEST EXAMPLE 1

The Effect of reducing lipid by the action of the compounds according to the present invention was measured as follows:

To each group of 5 to 6 Wister male rats weighing from 140 to 150 g, a test compound suspended in a 0.5% carboxymethylcellulose (CMC) solution was orally administrated by 10, 30 or 40 mg/kg once per day, for 5 days or 8 days. Blood was sampled three hours after the final administration of the test compound and the amount of triglycerides (TG) in serum was determined by an enzymatic method using a neutral fat measuring kit, New Clintec (TG) manufactured by Diatron Co., while the amount of cholesterol (Chol) was measured by another enzymatic method using a cholesterol determing kit, Determina-TC5 manufactured by Kyowa Medix Co. The reduction rates (%) were determined for each amount of TG and Chol in comparison with those of control group to which the test compound was not applied. The results are shown in Table 6 below (compound No. corresponds to those in Table 1).

TABLE 6

| Compound No. | Dose (mg/kg) | Administration Period (days) | TG Reduction (%) | Chol. Reduction (%) |
|---|---|---|---|---|
| 10 | 10 | 5 | 3.0 | 20.4 |
| 14 | " | " | 2.9 | 24.5 |
| " | 30 | " | 31.4 | 32.1 |
| 16 | 10 | " | 1.7 | 10.3 |
| 30 | 30 | 8 | 46.1 | 40.0 |
| 32 | " | " | 27.6 | 16.4 |
| 37 | 40 | " | 25.7 | 21.5 |
| 38 | 30 | " | 54.0 | 30.0 |
| 40 | 40 | " | 27.6 | 23.7 |
| 72 | 10 | 5 | 16.0 | 10.3 |
| 76 | 30 | 8 | 61.2 | 31.4 |
| 82 | 30 | 5 | 23.1 | 10.3 |
| 90 | " | " | 49.0 | 36.0 |
| 92 | " | " | 43.5 | 30.4 |
| 102 | " | " | 29.9 | 16.1 |
| 104 | " | " | 39.9 | 7.6 |

What is claimed is:

1. A pyrrolecarboxylic acid derivative represented by the following formula (I):

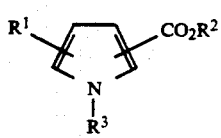

wherein $R^1$ is a hydrogen atom, an alkyl group of 10 to 16 carbon atoms,

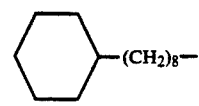

or an alkenyl group of 8 to 16 carbon atoms, $R^2$ is a hydrogen atom, a phenyl group, or an alkyl group of 1 to 10 carbon atoms unsubstituted or substituted with a halogen atom, hydroxyl group, amino group, alkylamino group of 1 to 5 carbon atoms, carbamoyl group, $C_1$-$C_5$-alkylcarbonylamino group, alkylthio group of 1 to 5 carbon atoms, mercapto group, a $C_1$-$C_5$-alkylcarbonyloxy group of aminocarbonyloxy group, and $R^3$ is an alkyl group of 10 to 16 carbon atoms or an alkenyl group of 10 to 16 carbon atoms, provided that, when $R^1$ is a group other than a hydrogen atom, $R^1$ is not adjacent to $CO_2R^2$, or a pharmaceutically acceptable salt thereof.

2. The compound of claim 1, wherein $R^2$ is a hydrogen atom, a phenyl group or a linear or branched alkyl group of 1 to 4 carbon atoms unsubstituted or substituted with a halogen atom, hydroxyl group, amino group, alkylamino group of 1 to 5 carbon atoms, carbamoyl group, $C_1$-$C_5$ -alkylcarbonylamino group, alkylthio group of 1 to 5 carbon atoms, mercapto group, $C_1$-$C_5$-alkylcarbonyloxy group or aminocarbonyloxy group.

3. A pharmaceutical composition for treating hyperlipemia and/or arteriosclerosis, comprising: a therapeutically effective amount of a pyrrolecarboxylic acid derivative represented by the formula (I):

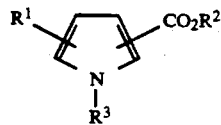

wherein $R^1$ is a hydrogen atom, an alkyl group of 10 to 16 carbon atoms, or an alkenyl group of 8 to 16 carbon atoms, $R^2$ is a hydrogen atom, a phenyl group, or an alkyl group of 1 to 10 carbon atoms unsubstituted or substituted with a halogen atom, hydroxyl group, amino group, alkylamino group of 1 to 5 carbon atoms, carbamoyl group, $C_1$-$C_5$-alkylcarbonylamino group, alkylthio group of 1 to 5 carbon atoms, mercapto group, a $C_1$-$C_5$-alkylcarbonyloxy group or aminocarbonyloxy group, and $R^3$ is an alkyl group of 10 to 16 carbon atoms or an alkenyl group of 10 to 16 carbon atoms, provided that, when $R^1$ is a group other than a hydrogen atom, $R^1$ is not adjacent to $CO_2R^2$, or a pharmaceutically acceptable salt thereof, in admixture with a pharmaceutically acceptable carrier or diluent.

4. A pyrrolecarboxylic acid derivative represented by the following formula:

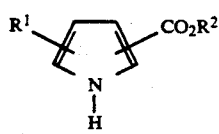
(I')

wherein $R^1$ is an alkyl group of 10 to 16 carbon atoms,

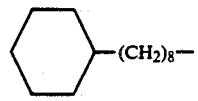

or an alkenyl group of 10 to 16 carbon atoms and $R^2$ is a hydrogen atom, a phenyl group, or an alkyl group of 1 to 10 carbon atoms unsubstituted or substituted with a halogen atom, hydroxyl group, amino group, alkylamino group of 1 to 5 carbon atoms, carbamoyl group, $C_1$-$C_5$-alkylcarbonylamino group, alkylthio group of 1 to 5 carbon atoms, mercapto group, a $C_1$-$C_5$-alkylcarbonyloxy group or aminocarbonyloxy group, provided that $R^1$ is not adjacent to $CO_2R^2$, or a pharmaceutically acceptable salt thereof.

5. A pyrrolecarboxylic acid derivative or a pharmaceutically acceptable salt thereof as defined in claim 4, wherein $R^2$ is a hydrogen atom, a phenyl group or an alkyl group of 1 to 5 carbon atoms unsubstituted or substituted with a halogen atom, hydroxyl group, alkylamino group of 1 to 5 carbon atoms or alkylthio group of 1 to 5 carbon atoms.

6. A pyrrolecarboxylic acid derivative or a pharmaceutically acceptable salt thereof as defined in claim 4, wherein $R^2$ is a hydrogen atom, a phenyl group or an alkyl group of 1 to 5 carbon atoms.

7. A pyrrolecarboxylic acid derivative or a pharmaceutically acceptable salt thereof as defined in claim 4, wherein $R^2$ is a hydrogen atom or an alkyl group of 1 to 5 carbon atoms.

8. A pyrrolecarboxylic acid derivative or a pharmaceutically acceptable salt thereof as defined in claim 4, wherein $R^1$ is an alkyl group of 10 to 16 carbon atoms.

9. A pyrrolecarboxylic acid derivative or a pharmaceutically acceptable salt thereof as defined in claim 4, wherein $R^2$ is hydrogen atom.

10. A pharmaceutical composition for treating hyperlipemia and/or arteriosclerosis comprising a therapeutically effective amount of pyrrolecarboxylic acid derivative represented by the following formula (I'):

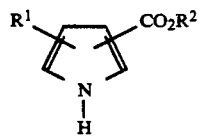
(I')

wherein $R^1$ is an alkyl group of 10 to 16 carbon atoms,

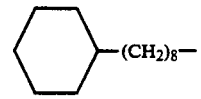

or an alkenyl group of 10 to 16 carbon atoms and $R^2$ is a hydrogen atom, a phenyl group, or an alkyl group of 1 to 5 carbon atoms unsubstituted or substituted with a halogen atom, hydroxyl group, amino group, alkylamino group of 1 to 5 carbon atoms, carbamoyl group, $C_1$-$C_5$-alkylcarbonylamino group, alkylthio group of 1 to 5 carbon atoms, mercapto group, a $C_1$-$C_5$-alkylcarbonyloxy group or aminocarbonyloxy group, provided that $R^1$ is not adjacent to $CO_2R^2$, or a pharmaceutically acceptable salt thereof, in admixture with a pharmaceutically acceptable carrier of diluent.

11. The derivative of claim 1, wherein $R^1$ is alkenyl of 10 to 16 carbon atoms.

12. The composition of claim 3, wherein $R^1$ is alkenyl of 10 to 16 carbon atoms.

* * * * *